United States Patent
Dietz et al.

(10) Patent No.: US 9,138,440 B2
(45) Date of Patent: Sep. 22, 2015

(54) METHODS FOR USING MIFEPRISTONE TO REDUCE THE NUMBER OF CD14+/DR-MONOCYTES

(75) Inventors: Allan B. Dietz, Chatfield, MN (US); Peggy A. Bulur, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 12 days.

(21) Appl. No.: 14/006,536

(22) PCT Filed: Apr. 5, 2012

(86) PCT No.: PCT/US2012/032321
§ 371 (c)(1),
(2), (4) Date: Sep. 20, 2013

(87) PCT Pub. No.: WO2012/138857
PCT Pub. Date: Oct. 11, 2012

(65) Prior Publication Data
US 2014/0011790 A1    Jan. 9, 2014

Related U.S. Application Data

(60) Provisional application No. 61/473,414, filed on Apr. 8, 2011.

(51) Int. Cl.
*A61K 31/567* (2006.01)
(52) U.S. Cl.
CPC .................................. *A61K 31/567* (2013.01)
(58) Field of Classification Search
None
See application file for complete search history.

(56) References Cited

U.S. PATENT DOCUMENTS

2007/0060546 A1*  3/2007  Ruat et al. ........................ 514/63
2010/0196266 A1*  8/2010  Goldenberg et al. ........ 424/1.49

FOREIGN PATENT DOCUMENTS

EP         1278523         7/2004
WO    WO 2005/023179      3/2005

OTHER PUBLICATIONS

International Search Report and Written Opinion in International Application No. PCT/US2012/032321, mailed Oct. 12, 2012, 5 pages.

(Continued)

*Primary Examiner* — Anna Pagonakis
(74) *Attorney, Agent, or Firm* — Fish & Richardson P.C.

(57) ABSTRACT

This document provides methods and materials involved in reducing suppression of immune function in mammals. For example, methods and materials for (a) identifying a mammal as having an elevated level of CD14+/DR− cells (e.g., CD14+/DR− monocytes) and (b) administering RU486 (mifepristone; or drugs with a similar functional profile) to the identified mammal under conditions that change the ratio of CD14+/HLA-DR− cells to CD14+/HLA-DR+ cells as well as methods and materials for (a) identifying a mammal as being likely to experience an elevated level of CD14+/DR− cells (e.g., CD14+/DR− monocytes) and (b) administering RU486 (mifepristone; or drugs with a similar functional profile) to the identified mammal under conditions that reduce the degree to which the mammal develops CD14+/DR− cells are provided.

18 Claims, 1 Drawing Sheet

(56) References Cited

OTHER PUBLICATIONS

International Preliminary Report on Patentability in International Application No. PCT/US2012/032321, mailed Oct. 17, 2013, 5 pages.

Antoniades et al., "Reduced monocyte HLA-DR expression: a novel biomarker of disease severity and outcome in acetaminophen-induced acute liver failure," Hepatology, 2006, 44:34-43.

Check et al., "Efficacy of the progesterone receptor antagonist mifepristone for palliative therapy of patients with a variety of advanced cancer types," Anticancer Research, 2010, 30(2):623-628.

Check et al., "Support for the hypothesis that successful immunotherapy of various cancers can be achieved by inhibiting a progesterone associated immunomodulatory protein," Medical Hypotheses, 2009, 72(1):87-90.

Cleland et al., "Ectopic pregnancy and emergency contraceptive pills: a systematic review," Obstetrics & Gynecology, 2010, 115(6):1263-1266.

Gustafson et al., "Systemic immune suppression in glioblastoma: the interplay between CD14+HLA-DRlo/neg monocytes, tumor factors, and dexamethasone," Neuro-Oncology, 2010, 12(7):631-644.

Hershman et al., "Monocyte HLA-DR antigen expression characterizes clinical outcome in the trauma patient," Br J Surg., 1990, 77(2):204-207.

Ho et al., "A strong association between down-regulation of HLA-DR expression and the late mortality in patients with severe acute pancreatitis," Am J Gastroenterol., 2006, 101(5):1117-1124.

Johanssen and Allolio, "Mifepristone (RU 486) in Cushing's Syndrome," Eur J Endocrinol., 2007, 157(5):561-569.

Kim et al., "Differential down-regulation of HLA-DR on monocyte subpopulations during systemic inflammation," 2010, Critical Care, 14:R61, 12 pages.

Kling et al., "Glucocorticoid inhibition in the treatment of depression: can we think outside the endocrine hypothalamus?" Depression & Anxiety, 2009, 26(7):641-649.

Lin et al., "Immunosuppressive CD14+HLA-DRlow/– monocytes in Bcell non-Hodgkin lymphoma," Blood, 2011, 117(3):872-881.

Nihalani and Schwartz, "Mifepristone, a glucocorticoid antagonist for the potential treatment of psychotic major depression," Current Opinion in Investigational Drugs, 2007, 8(7):563-569.

Pecci et al., "New lead compounds in the search for pure antiglucocorticoids and the dissociation of antiglucocorticoid effects," J Steroid Biochem Mol Biol., 2009, 113(3-5):155-162.

Rodrigues et al., "Normal human monocytes exposed to glioma cells acquire myeloid derived suppressor cell-like properties," Neuro-Oncology, 2010, 12(4):351-365.

Satoh et al., "Human leukocyte antigen-DR expression on peripheral monocytes as a predictive marker of sepsis during acute pancreatitis," Pancreas, 2002, 25(3):245-250.

Vuk-Pavolvic et al., "Immunosuppressive $CD14^+HLA-DR^{low/}$ monocytes in prostate cancer," Prostate, 2010, 70:443-455.

Wasmuth et al., "Patients with acute on chronic liver failure display "sepsis-like" immune paralysis," J Hepatol., 2005, 42(2):195-201.

Weiss et al., "Effect of ethanol on B cell expression of major histocompatibility class II proteins in immunized mice," Immunopharmacol., 1998, 39:61-72.

Yeager et al., "In vivo exposure to high or low cortisol has biphasic effects on inflammatory response pathways of human monocytes," Anesth Analg., Nov. 2008, 107(5):1726-1734.

Young, "Antiglucocoticoid treatments for depression," Australian & New Zealand J Psychiatry, 2006, 40(5):402-405.

Zhang et al., "Restraint stress-induced immunosuppression by inhibiting leukocyte migration and Th1 cytokine expression during the intraperitoneal infection of Listeria monocytogenes," J Neuroimmunol., 1998, 92:139-151.

Zhou et al., "Corticosterone exerts immunostimulatory effects on macrophages via endoplasmic reticulum stress," Br J Surg., 2010, 97:281-293.

* cited by examiner

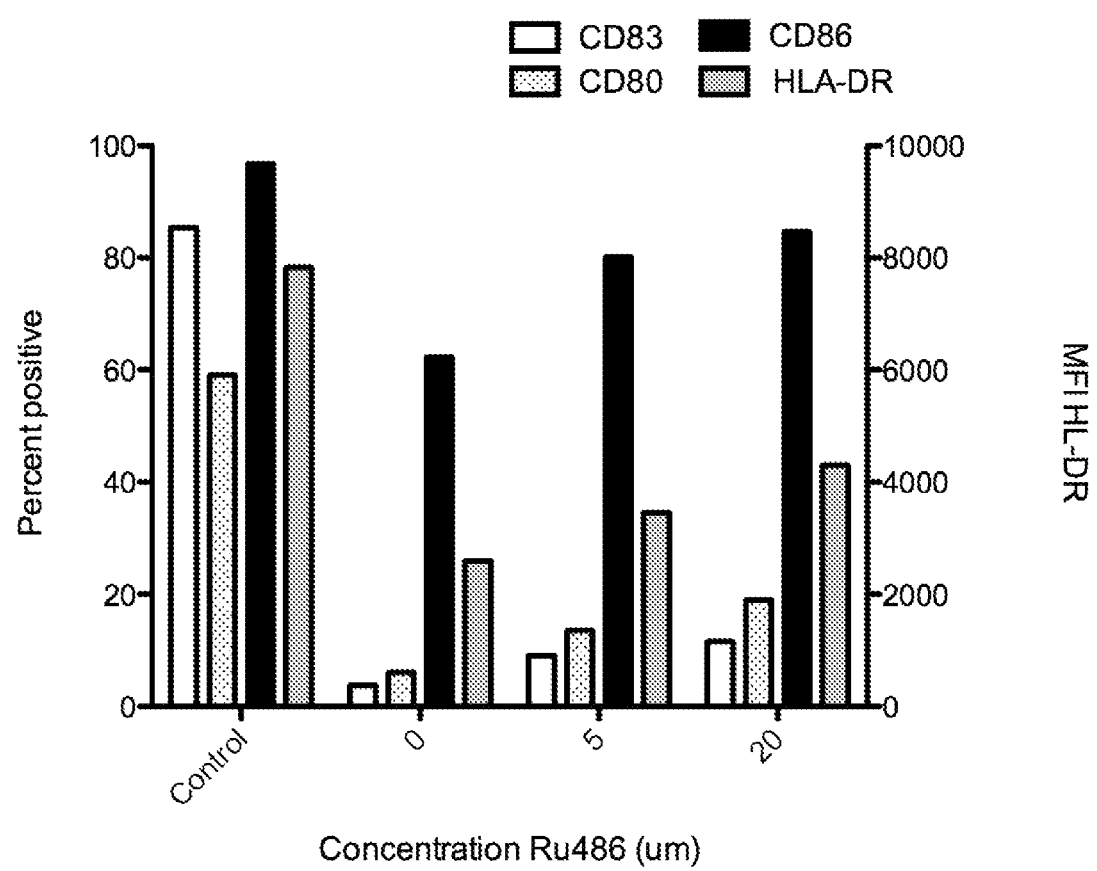

METHODS FOR USING MIFEPRISTONE TO REDUCE THE NUMBER OF CD14+/DR-MONOCYTES

CROSS-REFERENCE TO RELATED APPLICATIONS

This application is a National Stage application under 35 U.S.C. 371 of International Application No. PCT/US2012/032321, having an International Filing Date of Apr. 5, 2012, which claims the benefit of U.S. Provisional Application Ser. No. 61/473,414, filed Apr. 8, 2011. The disclosure of the prior application is considered part of (and is incorporated by reference in) the disclosure of this application.

BACKGROUND

1. Technical Field

This document relates to methods and materials involved in reducing suppression of immune function in mammals. For example, this document provides methods and materials for (a) identifying a mammal as having an elevated level of $CD14^+/HLA\text{-}DR^-$ cells (e.g., $CD14^+/HLA\text{-}DR^-$ monocytes) and (b) administering RU486 (mifepristone) to the identified mammal under conditions that change the ratio of $CD14^+/HLA\text{-}DR^-$ cells to $CD14^+/HLA\text{-}DR^+$ cells. This document also provides methods and materials for (a) identifying a mammal as being likely to experience an elevated level of $CD14^+/HLA\text{-}DR^-$ cells (e.g., $CD14^+/HLA\text{-}DR^-$ monocytes) and (b) administering RU486 (mifepristone) to the identified mammal under conditions that reduce the degree to which the mammal develops $CD14^+/HLA\text{-}DR^-$ cells.

2. Background Information

The immune system of a mammal is a system of biological structures and processes that helps protect the mammal from diseases by identifying and killing pathogens and tumor cells. A monocyte is one type of white blood cell that is part of the immune system. Monocytes can have several roles in the immune system. For example, monocytes can migrate to sites of infection and differentiate into macrophages and dendritic cells. Alternatively, monocytes can differentiate into agents acting to suppress immunity characterized by the loss of HLA-DR (or DR for short), an HLA class II marker.

SUMMARY

This document provides methods and materials involved in reducing suppression of immune function in mammals. For example, this document provides methods and materials for (a) identifying a mammal as having an elevated level of $CD14^+/DR^-$ cells (e.g., $CD14^+/DR^-$ monocytes) and (b) administering RU486 (mifepristone) to the identified mammal under conditions that change the ratio of $CD14^+/DR^-$ cells to $CD14^+/DR^+$ cells such that as a ratio there are less $CD14^+/DR^-$ cells relative to $CD14^+/DR^+$ cells. While not being limited to any particular mode of action, the administration of RU486 can alter the ratio of $CD14^+/DR^-$ cells to $CD14^+/DR^+$ cells through changes in polypeptide expression (e.g., an increase in HLA-DR polypeptide expression by at least a portion of the mammal's $CD14^+/DR^-$ cells), altered differentiation, or selective killing (e.g., killing of more $CD14^+/DR^-$ cells than killing of $CD14^+/DR^+$ cells). Having the ability to reduce the number of $CD14^+/DR^-$ cells or the ratio of $CD14^+/DR^-$ cells to $CD14^+/DR^+$ cells within a mammal can allow clinicians and patients to reduce the immunosuppressive effects caused by $CD14^+/DR^-$ cells. In some cases, reducing the number of $CD14^+/DR^-$ cells or the ratio of $CD14^+/DR^-$ cells to $CD14^+/DR^+$ cells within a mammal can result in enhanced immune function within a mammal.

This document also provides methods and materials for (a) identifying a mammal as being likely to experience an elevated level of $CD14^+/DR^-$ cells (e.g., $CD14^+/DR^-$ monocytes) and (b) administering RU486 (mifepristone) to the identified mammal under conditions that reduce the degree to which the mammal develops $CD14^+/DR^-$ cells. Having the ability to reduce the number of $CD14^+/DR^-$ cells that may develop within a mammal can allow clinicians and patients to reduce the immunosuppressive effects that can occur when a mammal develops an increased number of $CD14^+/DR^-$ cells. In some cases, reducing the number of $CD14^+/DR^-$ cells that may develop within a mammal can result in the mammal experiencing an enhanced immune function as compared to the level of immune function the mammal would experience had more $CD14^+/DR^-$ cells been allowed to develop.

As described herein, treating cells with RU486 while the cells are exposed to conditions that result in formation of $CD14^+/DR^-$ cells can result in the development of less $CD14^+/DR^-$ cells. Having the ability to reduce the number of $CD14^+/DR^-$ cells that develop can enhance immune function for patients such as major surgery patients, burn victim patients, patients undergoing chemotherapy and/or radiation treatment, sepsis patients, patients suffering from an infectious disease, and cancer patients. In some cases, having the ability to reduce the number of $CD14^+/DR^-$ cells that develop can enhance immune function and allow clinicians to treat various medical conditions such as cancer, sepsis, and infectious diseases more effectively.

In general, one aspect of this document features a method for reducing the number of $CD14^+/DR^-$ cells or the ratio of $CD14^+/DR^-$ cells to $CD14^+/DR^-$ cells of within a mammal. The method comprises, or consists essentially of, (a) identifying a mammal as having an elevated level of $CD14^+/DR^-$ cells, and (b) administering mifepristone to the mammal under conditions wherein the number of $CD14^+/DR^-$ cells or the ratio of $CD14^+/DR^-$ cells to $CD14^+/DR^+$ cells within the mammal is reduced. The mammal can be a human. The mammal can have sepsis or cancer. The elevated level of $CD14^+/DR^-$ cells can be a level wherein greater than 10 percent (e.g., greater than 13.5 percent or greater than 15 percent) of $CD14^+$ cells are $CD14^+/DR^-$ cells. The mifepristone can be administered in an amount, at a frequency, and for a duration effective to reduce the number of $CD14^+/DR^-$ cells within the mammal by at least 10 percent. The amount can be between about 4 mg and about 200 mg per day. The frequency can be between about once a day to about once a week. The duration can be between about one day and about three months. The number of $CD14^+/DR^-$ cells within the mammal can be reduced by at least 10 percent. The number of $CD14^+/DR^-$ cells within the mammal can be reduced by at least 20 percent. The $CD14^+/DR^-$ cells can be $CD14^+/DR^-$ monocytes.

In another aspect, this document features a method for reducing the number of $CD14^+/DR^-$ cells that may be develop in a mammal. The method comprises, or consists essentially of, (a) identifying a mammal as being likely to experience an elevated level of $CD14^+/DR^-$ cells, and (b) administering mifepristone to the mammal under conditions wherein the number of $CD14^+/DR^-$ cells developed within the mammal is reduced as compared to the number of $CD14^+/DR^-$ cells developed within a comparable mammal not treated with the mifepristone. The mammal can be a human. The mammal can have sepsis or cancer. The elevated level of $CD14^+/DR^-$ cells can be a level wherein greater than 10 percent (e.g., greater than 13.5 percent or greater than 15 percent) of $CD14^+$ cells are $CD14^+/DR^-$ cells. The mifepristone can be administered in an amount, at a frequency, and for a duration effective to reduce the number of CD14$^+$/DR$^-$ cells developed in the mammal by at least 10 percent as compared to the number of CD14$^+$/DR$^-$ cells developed within the comparable mammal. The amount can be between about 4 mg and about 200 mg per day. The frequency can be between about once a day to about once a week. The duration can be between about one day and about three months. The number of CD14$^+$/DR$^-$ cells developed within the mammal can be reduced by at least 10 percent as compared to the number of CD14$^+$/DR$^-$ cells developed within the comparable mammal. The number of CD14$^+$/DR$^-$ cells developed within the mammal can be reduced by at least 20 percent as compared to the number of CD14$^+$/DR$^-$ cells developed within the comparable mammal. The CD14$^+$/DR$^-$ cells can be CD14$^+$/DR$^-$ monocytes.

In another aspect, this document features a method for reducing the number of CD14$^+$/DR$^-$ cells or the ratio of CD14$^+$/DR$^-$ cells to CD14$^+$/DR$^-$ cells of within a mammal. The method comprises, or consists essentially of, administering, to a mammal identified as having an elevated level of CD14$^+$/DR$^-$ cells, mifepristone under conditions wherein the number of CD14$^+$/DR$^-$ cells or the ratio of CD14$^+$/DR$^-$ cells to CD14$^+$/DR$^+$ cells within the mammal is reduced. The mammal can be a human. The mammal can have sepsis or cancer. The elevated level of CD14$^+$/DR$^-$ cells can be a level wherein greater than 10 percent (e.g., greater than 13.5 percent or greater than 15 percent) of CD14$^+$ cells are CD14$^+$/DR$^-$ cells. The mifepristone can be administered in an amount, at a frequency, and for a duration effective to reduce the number of CD14$^+$/DR$^-$ cells within the mammal by at least 10 percent. The amount can be between about 4 mg and about 200 mg per day. The frequency can be between about once a day to about once a week. The duration can be between about one day and about three months. The number of CD14$^+$/DR$^-$ cells within the mammal can be reduced by at least 10 percent. The number of CD14$^+$/DR$^-$ cells within the mammal can be reduced by at least 20 percent. The CD14$^+$/DR$^-$ cells can be CD14$^+$/DR$^-$ monocytes.

In another aspect, this document features a method for reducing the number of CD14$^+$/DR$^-$ cells that may be develop in a mammal. The method comprises, or consists essentially of, administering, to a mammal identified as being likely to experience an elevated level of CD14$^+$/DR$^-$ cells, mifepristone under conditions wherein the number of CD14$^+$/DR$^-$ cells developed within the mammal is reduced as compared to the number of CD14$^+$/DR$^-$ cells developed within a comparable mammal not treated with the mifepristone. The mammal can be a human. The mammal can have sepsis or cancer. The elevated level of CD14$^+$/DR$^-$ cells can be a level wherein greater than 10 percent (e.g., greater than 13.5 percent or greater than 15 percent) of CD14$^+$ cells are CD14$^+$/DR$^-$ cells. The mifepristone can be administered in an amount, at a frequency, and for a duration effective to reduce the number of CD14$^+$/DR$^-$ cells developed in the mammal by at least 10 percent as compared to the number of CD14$^+$/DR$^-$ cells developed within the comparable mammal. The amount can be between about 4 mg and about 200 mg per day. The frequency can be between about once a day to about once a week. The duration can be between about one day and about three months. The number of CD14$^+$/DR$^-$ cells developed within the mammal can be reduced by at least 10 percent as compared to the number of CD14$^+$/DR$^-$ cells developed within the comparable mammal. The number of CD14$^+$/DR$^-$ cells developed within the mammal can be reduced by at least 20 percent as compared to the number of CD14$^+$/DR$^-$ cells developed within the comparable mammal. The CD14$^+$/DR$^-$ cells can be CD14$^+$/DR$^-$ monocytes.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 is a graph plotting the percent of CD14$^+$ cells that are positive for CD80, CD83, or CD86. The graph also plots the mean fluorescence intensity (MFI) for HLA-DR staining for the CD14$^+$ cells. Control cells were isolated CD14$^+$ cells that were cultured but not exposed to cancer cells or RU486. The 0, 5, and 20 labeled bars are for isolated CD14$^+$ cells exposed to cancer cells and treated with 0, 5, or 20 µM, respectively, of RU486.

DETAILED DESCRIPTION

This document provides methods and materials involved in reducing suppression of immune function in mammals. For example, this document provides methods and materials for (a) identifying a mammal as having an elevated level of CD14$^+$/DR$^-$ cells (e.g., CD14$^+$/DR$^-$ monocytes) and (b) administering RU486 (mifepristone) to the identified mammal under conditions that change the ratio of CD14$^+$/DR$^-$ cells to CD14$^+$/DR$^+$ cells such that as a ratio there are less CD14$^+$/DR$^-$ cells relative to CD14$^+$/DR$^+$ cells. This document also provides methods and materials for (a) identifying a mammal as being likely to experience an elevated level of CD14$^+$/DR$^-$ cells (e.g., CD14$^+$/DR$^-$ monocytes) and (b) administering RU486 (mifepristone) to the identified mammal under conditions that reduce the degree to which the mammal develops CD14$^+$/DR$^-$ cells.

Any type of mammal identified as having an elevated level of CD14$^+$/DR$^-$ cells (e.g., CD14$^+$/DR$^-$ monocytes) or as being likely to experience an elevated level of CD14$^+$/DR$^-$ cells (e.g., CD14$^+$/DR$^-$ monocytes) can be treated with RU486 as described herein. For example, humans, monkeys, cows, sheep, horses, dogs, cats, rats, and mice can be treated with RU486 to reduce the level of CD14$^+$/DR$^-$ cells (e.g., an absolute level of CD14$^+$/DR$^-$ cells or the ratio of CD14$^+$/DR$^-$ cells to CD14$^+$/DR$^+$ cells) or the degree of CD14$^+$/DR$^-$ cell development, thereby reducing suppression of immune function as the presence of elevated levels of CD14$^+$/DR$^-$ cells can result in general immune suppression. For example, CD14$^+$/DR$^-$ suppressive monocytes can contribute to systemic immune suppression, can prevent the differentiation of monocytes into antigen presenting cells, and can directly inhibit T cell function.

RU486 (mifepristone) is a progesterone receptor modulator and anti-glucocorticoid. In some cases, other progesterone receptor modulators such as Ulipristal acetate, Asoprisnil, and CDB-4124 can be used alone or in combination with other anti-glucocorticoids such as cyproterone, progesterone, and/or DHEA as described herein as an alternative to RU486 or in addition to RU486.

As described herein, RU486 can prevent or at least partially inhibit the conversion of normal monocytes into suppressive monocytes or can re-program or re-direct differentiation of at least some suppressive monocytes back into normal monocytes or immune stimulating cells such as dendritic cells. In some cases, RU486 can be used as a prophylactic to prevent or at least partially inhibit the differentiation of suppressive monocytes for conditions where suppressive monocytes may occur (e.g., trauma, major surgery, burns, chemotherapy, radiation treatment, cancer, or sepsis). In some cases, RU486 can be used as supportive care to conditions with suppressive monocytes to prevent or at least partially inhibit additional generation of suppressive monocytes. In some cases, RU486 can be used to treat conditions with severe levels of suppressive monocytes to reduce or eliminate the existence of suppressive monocytes or to restore pro-inflammatory/pro-immune function to the monocytes in cases where patients are undergoing other treatments. Such conditions can include, without limitation, conditions where the patient has sepsis, cancer, trauma, burns, or an infectious disease.

Any appropriate method can be used to identify a mammal as having an elevated level of $CD14^+/DR^-$ cells (e.g., $CD14^+/DR^-$ monocytes) or as being likely to experience an elevated level of $CD14^+/DR^-$ cells (e.g., $CD14^+/DR^-$ monocytes). For example, the level of $CD14^+/DR^-$ cells within a mammal having or suspected of having or developing a particular medical condition (e.g., cancer, sepsis, autoimmunity, trauma, or infection) can be determined and compared to cut-off values of $CD14^+/DR^-$ cells for that particular condition or values obtained from healthy volunteers to assess whether the level is a normal level, an elevated level (e.g., a high level of $CD14^+/DR^-$ cells), or a reduced level (e.g., a low level of $CD14^+/DR^-$ cells). It is noted that healthy volunteers can have an average of about 8.5±2.5 percent of all $CD14^+$ cells within a blood sample as $DR^-$. In some cases, an elevated level of $CD14^+/DR^-$ cells can be any level that indicates that greater than about 12 percent (e.g., greater than about 13 percent, greater than about 13.5 percent, greater than about 14 percent of $CD14^+$ cells, greater than about 15 percent, or greater than about 16 percent) within the circulating blood of a mammal are $DR^-$.

The level of $CD14^+/DR^-$ cells can be determined using a sample (e.g., a blood sample) obtained from the mammal to be assessed. Once obtained, the sample can be treated such that the level of $CD14^+/DR^-$ cells can be determined. Standard cell staining and immunoflourescence techniques (e.g., flow cytometry) can be used to determine the level of $CD14^+/DR^-$ cells. For example, anti-CD14 and anti-HLA-DR antibodies can be used to perform flow cytometry in order to determine the level of $CD14^+/DR^-$ cells present within a sample. In some cases, nucleic acid-based assays can be used to assess the level of $CD14^+/DR^-$ cells. For example, the amount of particular transcripts (e.g., CD14 or DR transcripts) can be determined in whole blood using techniques such as quantitative PCR.

Once the level of $CD14^+/DR^-$ cells is determined to be an elevated level for a mammal (e.g., an elevated level of $CD14^+/DR^-$ cells as determined by an elevated ratio of $CD14^+/DR^-$ cells to $CD14^+/DR^-$ cells), the mammal can be treated with RU486 as described herein. In some cases, a mammal suspected to develop an elevated level of $CD14^+/DR^-$ cells can be treated with RU486 as described herein. A composition containing RU486 can be administered to a mammal using any appropriate route of administration including, without limitation, oral, intravenous, and intraperitoneal routes of administration. In addition, a composition containing RU486 can be administered to an identified mammal in an amount, at a frequency, and for a duration effective to change the ratio of $CD14^+/DR^-$ cells to $CD14^+/DR^+$ cells such that as a ratio there are less $CD14^+/DR^-$ cells relative to $CD14^+/DR^+$ cells. In some cases, a composition containing RU486 can be administered to an identified mammal in an amount, at a frequency, and for a duration effective reduce the degree to which the mammal develops $CD14^+/DR^-$ cells.

Effective doses can vary, as recognized by those skilled in the art, depending on the severity of the condition (e.g., level of $CD14^+/DR^-$ cells), the route of administration, the sex, age and general health condition of the subject, excipient usage, the possibility of co-usage with other therapeutic treatments, and the judgment of the treating physician.

An effective amount of a composition containing RU486 can be any amount that changes the ratio of $CD14^+/DR^-$ cells to $CD14^+/DR^+$ cells such that as a ratio there are less $CD14^+/DR^-$ cells relative to $CD14^+/DR^+$ cells, without producing significant toxicity to the mammal. In some cases, an effective amount of a composition containing RU486 can be any amount that reduces the degree to which the mammal develops $CD14^+/DR^-$ cells. For example, an effective amount of RU486 can be from about 2 mg/kg to about 10 mg/kg (e.g., from about 4 mg/kg to about 10 mg/kg, from about 4.5 mg/kg to about 10 mg/kg, from about 5 mg/kg to about 10 mg/kg, or from about 6 mg/kg to about 10 mg/kg). In some cases, between about 150 mg and about 250 mg (e.g., between about 175 mg and about 250 mg, between about 200 mg and about 250 mg, between about 150 mg and about 225 mg, between about 150 mg and about 200 mg, or about 200 mg) of RU486 can be administered to an average sized human (e.g., about 70 kg) daily for between one and 30 weeks (e.g., between two and 30 weeks, between three and 30 weeks, between four and 30 weeks, between four and 20 weeks, or 28 days). If a particular mammal fails to respond to a particular amount, then the amount of RU486 can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., level of $CD14^+/DR^-$ cells) may require an increase or decrease in the actual effective amount administered.

The frequency of administration can be any frequency that changes the ratio of $CD14^+/DR^-$ cells to $CD14^+/DR^+$ cells such that as a ratio there are less $CD14^+/DR^-$ cells relative to $CD14^+/DR^+$ cells, without producing significant toxicity to the mammal. In some cases, an effective frequency of administration can be a frequency that reduces the degree to which the mammal develops $CD14^+/DR^-$ cells. For example, the frequency of administration can be from about once a month to about once a day, or from about twice a month to about twice a day, or from about three times a week to about once a day. The frequency of administration can remain constant or can be variable during the duration of treatment. A course of treatment with a composition containing RU486 can include rest periods. For example, a composition containing RU486 can be administered daily over a four week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition may require an increase or decrease in administration frequency.

An effective duration for administering a composition containing RU486 can be any duration that changes the ratio of $CD14^+/DR^-$ cells to $CD14^+/DR^+$ cells such that as a ratio there are less $CD14^+/DR^-$ cells relative to $CD14^+/DR^+$ cells, without producing significant toxicity to the mammal. In some cases, an effective duration can be a duration that reduces the degree to which the mammal develops $CD14^+/DR^-$ cells. Thus, the effective duration can vary from several days to several weeks, months, or years. In general, the effective duration can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the condition being treated. In some cases, a composition containing RU486 can be administered to a mammal having cancer in combination with one or more cancer treatment agents such as cisplatin, radiation, or IL-2 or in combination with surgery. For example, a kidney cancer patient having an elevated level of $CD14^+/DR^-$ cells can be administered RU486 in combination with or in a treatment regimen with a kidney cancer treatment agent such as torisel, nexavar, sutent, or IL-2. For example, a glioblastoma cancer patient having an elevated level of $CD14^+/DR^-$ cells can be administered RU486 in combination with or in a treatment regimen with a glioblastoma treatment agent such temazolomide, radiation, or surgery.

The invention will be further described in the following examples, which do not limit the scope of the invention described in the claims.

EXAMPLES

Example 1

RU486 Reduces the Production of $CD14^+/DR^-$ Cells

Isolated $CD14^+$ cells were co-cultured for three days with a renal cell tumor line (ACHN) at a 1:10 ratio in DMEM supplemented with 5% HABS. Either 0, 5, or 20 μM of RU486 was added to the culture on day 0. After three days in culture, non-adherent cells were collected from each of the T-25 flasks, washed, and replated in Cellgenix medium containing GM-CSF for two days. After the two days, the non-adherent cells were collected, washed, and resuspended in Cellgenix medium containing GM-CSF, TNFα, and PGE2 for an additional two days to mature. Non-adherent matured cells were collected, washed, stained, and analyzed by flow cytometry using cell surface markers for CD14, CD80, CD83, CD86, and HLA-DR. Control cells were monocytes cultured in a similar manner, but not exposed to the cancer cell line cells and not treated with RU487.

Control monocytes not exposed to cancer cells exhibited HLA-DR expression, while cells exposed to cancer cells (and not treated with RU486) exhibited much less HLA-DR expression (FIG. 1). Cells exposed to cancer cells and treated with RU486 (5 or 20 μM) exhibited more HLA-DR expression than cells exposed to cancer cells and not treated with RU486 (FIG. 1). These results demonstrate that treatment with RU486 can interfere with the generation of immune suppressive monocytes.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing the number of $CD14^+/DR^-$ monocytes or the ratio of $CD14^+/DR^-$ monocytes to $CD14^+/DR^+$ monocytes within a mammal, wherein said method comprises:
  (a) performing a cell staining or immunofluorescence technique to identify a mammal as having a level of $CD14^+/DR^-$ monocytes wherein greater than 10 percent of $CD14^+$ monocytes are $CD14^+/DR^-$ monocytes, and
  (b) administering mifepristone to said mammal, wherein the number of $CD14^+/DR^-$ monocytes or the ratio of $CD14^+/DR^-$ monocytes to $CD14^+/DR^+$ monocytes within said mammal is reduced following said administration; wherein the mammal has kidney cancer.

2. The method of claim 1, wherein said mammal is a human.

3. The method of claim 1, wherein said level of $CD14^+/DR^-$ monocytes is a level wherein greater than 12 percent of $CD14^+$ monocytes are $CD14^+/DR^-$ monocytes.

4. The method of claim 1, wherein said mifepristone is administered in an amount, at a frequency, and for a duration effective to reduce the number of $CD14^+/DR^-$ monocytes within said mammal by at least 10 percent.

5. The method of claim 4, wherein said amount is between about 4 mg and about 200 mg per day.

6. The method of claim 4, wherein said frequency is between about once a day to about once a week.

7. The method of claim 4, wherein said duration is between about one day and about three months.

8. The method of claim 1, wherein the number of $CD14^+/DR^-$ monocytes within said mammal is reduced by at least 10 percent following said administration.

9. The method of claim 1, wherein the number of $CD14^+/DR^-$ monocytes within said mammal is reduced by at least 20 percent following said administration.

10. A method for reducing the number of $CD14^+/DR^-$ monocytes or the ratio of $CD14^+/DR^-$ monocytes to $CD14^+/DR^+$ monocytes within a mammal, wherein said method comprises administering mifepristone to a mammal identified as having a level of $CD14^+/DR^-$ monocytes wherein greater than 10 percent of $CD14^+$ monocytes are $CD14^+/DR^-$ monocytes, wherein the number of $CD14^+/DR^-$ monocytes or the ratio of $CD14^+/DR^-$ monocytes to $CD14^+/DR^+$ monocytes within said mammal is reduced following said administration; wherein the mammal has kidney cancer.

11. The method of claim 10, wherein said mammal is a human.

12. The method of claim 10, wherein said level of $CD14^+/DR^-$ monocytes is a level wherein greater than 12 percent of $CD14^+$ monocytes are $CD14^+/DR^-$ monocytes.

13. The method of claim 10, wherein said mifepristone is administered in an amount, at a frequency, and for a duration effective to reduce the number of $CD14^+/DR^-$ monocytes within said mammal by at least 10 percent.

14. The method of claim 13, wherein said amount is between about 4 mg and about 200 mg per day.

15. The method of claim 13, wherein said frequency is between about once a day to about once a week.

16. The method of claim 13, wherein said duration is between about one day and about three months.

17. The method of claim 10, wherein the number of $CD14^+/DR^-$ monocytes within said mammal is reduced by at least 10 percent following said administration.

18. The method of claim 10, wherein the number of $CD14^+/DR^-$ monocytes within said mammal is reduced by at least 20 percent following said administration.

* * * * *